US00PP25949P2

(12) United States Plant Patent
Kordes

(10) Patent No.: US PP25,949 P2
(45) Date of Patent: Sep. 29, 2015

(54) HYBRID TEA ROSE PLANT NAMED 'KOR991658'

(50) Latin Name: *Rosa hydrida*
Varietal Denomination: KOR991658

(71) Applicant: Tim-Hermann Kordes, Klein Offenseth-Sparrieshoop (DE)

(72) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 194 days.

(21) Appl. No.: 13/998,460

(22) Filed: Nov. 1, 2013

(51) Int. Cl.
*A01H 5/02* (2006.01)

(52) U.S. Cl.
USPC ..... Plt./137

(58) Field of Classification Search
USPC ..... Plt./137
See application file for complete search history.

*Primary Examiner* — Anne Grunberg

(57) ABSTRACT

A new and distinct variety of rose with long lasting, novel apricot flowers, and attractive foliage. It exhibits upright to bushy growth with abundant flowers. The new variety propagates well by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KOR991658'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 1999. The crossing was between an un-named seedling, the seed parent, and another un-named seedling, the pollen parent by the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KOR991658'.

SUMMARY OF THE INVENTION

The new rose plant may be distinguished from its seed parent, an un-named seedling, by the following combination of characteristics:

1. 'KOR991658' has apricot flowers, whereas the un-named seedling has yellow flowers.
2. 'KOR991658' has a very double petal count, whereas the un-named seedling has a double petal count.

The new rose plant may be distinguished from its pollen parent, an un-named seedling, by the following combination of characteristics:

1. 'KOR991658' has apricot flowers, whereas the un-named seedling has yellow flowers.
2. 'KOR991658' has upright to bushy habit, whereas the un-named seedling has a compact and bushy habit.

The objective of the hybridization was to create a new and distinct rose plant with unique qualities, such as:

1. Uniform growth and flowering;
2. Abundant attractive, recurrent flowers;
3. Attractive and abundant foliage; and
4. Resistance to diseases encountered in landscapes and gardens.

This combination of qualities is not present in prior rose cultivars known to the inventor. These objectives have been substantially achieved and in that distinguish 'KOR991658' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KOR991658' was selected in 2005 from the seedling beds to be asexually propagated for further evaluation. The first asexual propagation of 'KOR991658' was done by budding in 2007 at the inventor's nursery in Offenseth-Sparrieshoop, Germany.

These initial and other subsequent propagations conducted in controlled environments demonstrate that 'KOR991658' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KOR991658'.

DETAILED BOTANICAL DESCRIPTION

The following is a description of 'KOR991658', as observed growing in September 2013 in a nursery in Jackson County, Oreg. on plants of 5 years of age. Color references are made using The Royal Horticultural Society (London, England) Colour Chart, 2001 except where common terms of color are used.

For a comparison, several physical characteristics of the rose variety 'KORtiglo', a rose variety from the same inventor described and illustrated in U.S. Plant Pat. No. 19,385 and issued on Oct. 28, 2008 are compared to 'KOR991658' in Chart 1.

CHART 1

| Characteristic | 'KOR991658' | 'KORtiglo' |
|---|---|---|
| Petal count | 50-55 | 100-120 |
| Number of leaflets | 7 | 3-5 |
| Flower general tonality | Orange Group 29C to Orange Group 29D | Yellow-Orange Group 20C |

Parents:

*Seed parent*.—An un-named seedling.

*Pollen parent*.—An un-named seedling.

Classification:

*Botanical classification*.—*Rosa hybrida* 'KOR991658'.

*Commercial classification*.—Hybrid Tea rose.

Flower and Flower Bud

Blooming habit: Recurrent.

Flower bud:

*Size*.—Upon opening, 25 mm in length from base of receptacle to distal end of bud and 15 mm diameter at its widest point.

*Bud form*.—Short. Pointed ovoid.

*Bud color*.—As sepals first unfold, bud color is Red Group 39A & Red Group 39B. When ¼ open, the upper surface of petals is Red Group 36B, and the lower surface is Red Group 37C and Red Group 37D.

*Sepals*.—Color: Upper surface: Yellow-Green Group 144B. Lower surface: Yellow-Green Group 144A. Size: Average 30-35 mm (l)×11-13 mm (w). Shape: Moderate foliaceous appendages on 3 of the five sepals. Apex: Apiculate. Base: Flat at union with receptacle. Quantity: Five. Surface texture: Upper side: Very pubescent. Lower surface: Somewhat pubescent. Stipitate glands: Limited numbers along margins.

Flower bloom:

*Fragrance*.—Light.

*Duration*.—On the plant 12-14 days. As a cut flower, 8-10 days. Senesced petals drop away cleanly.

*Size*.—Medium to large for a hybrid tea rose. When open, the average flower diameter is 85-90 mm and the average flower height is 45-50 mm.

*Form*.—Shape of flower when viewed from the side: Upon opening, upper part: Flat. Upon opening, lower part: Concave. Open flower, upper part: Flattened convex. Open flower, lower part: Concave.

Color:

*Upon opening, petals*.—Outermost petals: Outer Side: Basal zone: Red-Orange Group 20C. Middle zone: Orange Group 27A. Marginal zone: Red Group 36C. Inner Side: Basal zone: Yellow Group 11B. Middle and marginal zones: Red Group 36D. Innermost petals: Outer Side: Basal zone: Yellow Group 12C. Middle and marginal zones: Orange Group 25D. Inner Side: Basal zone: Yellow Group 12B. Middle and marginal zones: Yellow-Orange Group 22D.

*Upon opening, basal petal spots*.—Basal petal spot, outermost petals: Outer Side: Yellow Group 4C. Inner Side: Yellow Group 12A. Basal petal spot, innermost petals: Outer Side: No distinctive coloration at petal base observed. Inner Side: Yellow Group 12A.

*After opening, petals*.—Outermost petals: Outer Side: Red Group 56A. Inner Side: Red Group 56D. Innermost petals: Outer Side: Yellow-Orange Group 23D with Orange Group 29D in the margins. Inner Side: Yellow-Orange Group 19D.

*After opening, basal petal spots*.—Basal petal spot, outermost petals: Outer Side: Yellow Group 2D. Inner Side: Yellow Group 3C. Basal petal spot, innermost petals: Outer Side: Yellow Group 4A. Inner Side: Yellow Group 8A.

General tonality: On open flower Orange Group 29C to Orange Group 29D. No change in the general tonality at the end of the 4$^{th}$ day. Afterwards, general tonality is Orange Group 27D.

Petals:

*Petal count*.—Very Double.

*Average range*.—Approximately 50-55 petals under normal conditions.

*Petal reflex*.—Petals reflex slightly.

*Petal margin*.—Entire.

*Petal shape*.—Obovate to orbicular. Apex: Obtuse. Base: Obtuse to slightly cuneate.

*Petal size*.—35-50 mm (l)×35-50 mm (w).

*Thickness*.—Average.

*Petal arrangement*.—Not formal.

*Texture*.—Upper side: Smooth. Lower side: Slightly leathery.

Petaloids:

*Petaloid count*.—Average of 5-8 per flower.

*Petaloid size*.—25-30 mm (l)×20-25 mm (w).

*Petaloid color*.—Inner side: Orange Group 24D. Outer side: Orange Group 29A and Orange Group 29C.

*Petaloid texture*.—Upper side: Smooth. Lower side: Leathery.

*Margins*.—Entire to indented.

*Petaloid shape*.—Most commonly obovate to spatulate with some petaloids highly irregular. Apex: Obtuse. Base: Attenuate.

Reproductive organs:

*Pistils*.—Abundant. Approximately 70-75 present. Stigmas: Location: At the same position as the anthers. Color: Yellow Group 7A. Styles: Length: About 15 mm long. Color: Green-White Group 157A.

*Stamens*.—Approximately 120-130 on average and regularly arranged. Anthers: Size: Average 2 mm (l)×1 mm (w). Color: Greyed-Yellow Group 160D. Pollen: Generally present. Color: Greyed-Orange Group N163C. Filaments: Color: Yellow-Orange Group 16A. Length: 10-12 mm.

*Receptacle*.—Surface: Glabrous. Color: Yellow-Green Group 144A with intonations of Greyed-Purple Group 183C. Shape: Urn-shaped. Texture: Smooth. Size: 10 mm (h)×18 mm (w).

*Pedicel*.—Surface: With a few fine hairs. Length: 50-55 mm average length. Diameter: 4-4.5 mm average diameter. Color: Yellow-Green Group 144A with intonations of Greyed-Purple Group 183C. Strength:

Strong. Texture: Smooth. Borne: Multiple flower buds per stem, generally 1 to 2. Flowers held upright.

*Peduncle*.—Length: 70-75 mm average length. Diameter: 4-4.5 mm average diameter. Color: Yellow-Green Group 144A. Strength: Strong.

The Plant

Growth: Moderately vigorous.

Plant habit: Upright to bushy. When grown as a field plant, the average plant height is 100 cm and the average plant width is 60 cm.

Stems:

*Stem color*.—Young wood: Yellow-Green Group 144A. Older wood: Yellow-Green Group 146C.

*Intonations*.—Greyed-Purple Group 185A.

*Stem surface texture*.—Young wood: Smooth. Older wood: Rough.

Prickles: Present.

*Incidence*.—Average of 7-8 per each 10 cm of stem.

*Size*.—Average length: 6-8 mm.

*Color*.—Immature prickles: Yellow-Green Group 150D. Mature prickles: Yellow-Green Group 152D. Senescing to Greyed-Brown Group 199B.

*Anthocyanin*.—Greyed-Purple Group 185B.

*Shape*.—Concave.

Leaves: Normally 5-7 leaflets on normal leaves in middle of the stem.

*Venation pattern*.—Pyramidal net pattern.

*Leaf size*.—160 mm (l)×125 mm (w).

*Abundance*.—Average.

Leaflets:

*Size*.—Average size of the terminal leaflet is 75-80 mm (l)×45-50 mm (w).

*Shape*.—Elliptic. Base: Obtuse. Apex: Acute.

*Margins*.—Serrated.

*Surface*.—Upper side of leaflet: Semi-glossy. Under side of leaflet: Matte.

*Texture*.—Upper side of leaflet: Leathery. Under side of leaflet: Leathery.

*Color, mature foliage*.—Upper Leaflet Surface: Yellow-Green Group 147A. Lower Leaflet Surface: Yellow-Green Group 147B.

*Color, juvenile foliage*.—Upper Leaflet Surface: Green Group 137A. Lower Leaflet Surface: Green Group 137D.

*Anthocyanin intonation*.—Greyed-Purple Group 187B. Location: Juvenile foliage.

*Arrangement*.—Odd pinnate.

*Venation*.—Reticulate.

Stipules:

*Size*.—25 mm (l)×10 mm (w).

*Stipule color*.—Yellow-Green Group 147B.

*Stipitate glands*.—Abundant numbers along margins.

*Texture*.—Smooth.

*Shape*.—Apex: Apiculate. Base: Flat.

Petiole:

*Length*.—Average 30 mm.

*Diameter*.—Average 3 mm.

*Petiole color*.—Yellow-Green Group 146A. Underneath: Yellow-Green Group 146B.

*Margins*.—Limited numbers of stipitate glands.

*Prickles*.—Present.

*Texture*.—Smooth.

Petiole rachis:

*Length*.—Average 20 mm.

*Diameter*.—Average 2 mm.

*Color*.—Yellow-Green Group 146A.

*Margins*.—Limited numbers of stipitate glands.

*Prickles*.—A few small prickles underneath.

*Texture*.—Smooth.

Hips/seed formation: None observed.

Winter hardiness: To date, the variety has been grown successfully in Zone 6.

Disease resistance: Average resistance to Powdery mildew (*Sphaerotheca pannosa*), blackspot (*Diplocarpon rosae*), rust (*Phragmidium* sp.), and Botrytis (*Botrytis cinerea*) diseases under normal growing conditions in Jackson County, Oreg.

I claim:

1. A new and distinct variety of rose plant, as described and illustrated herein.

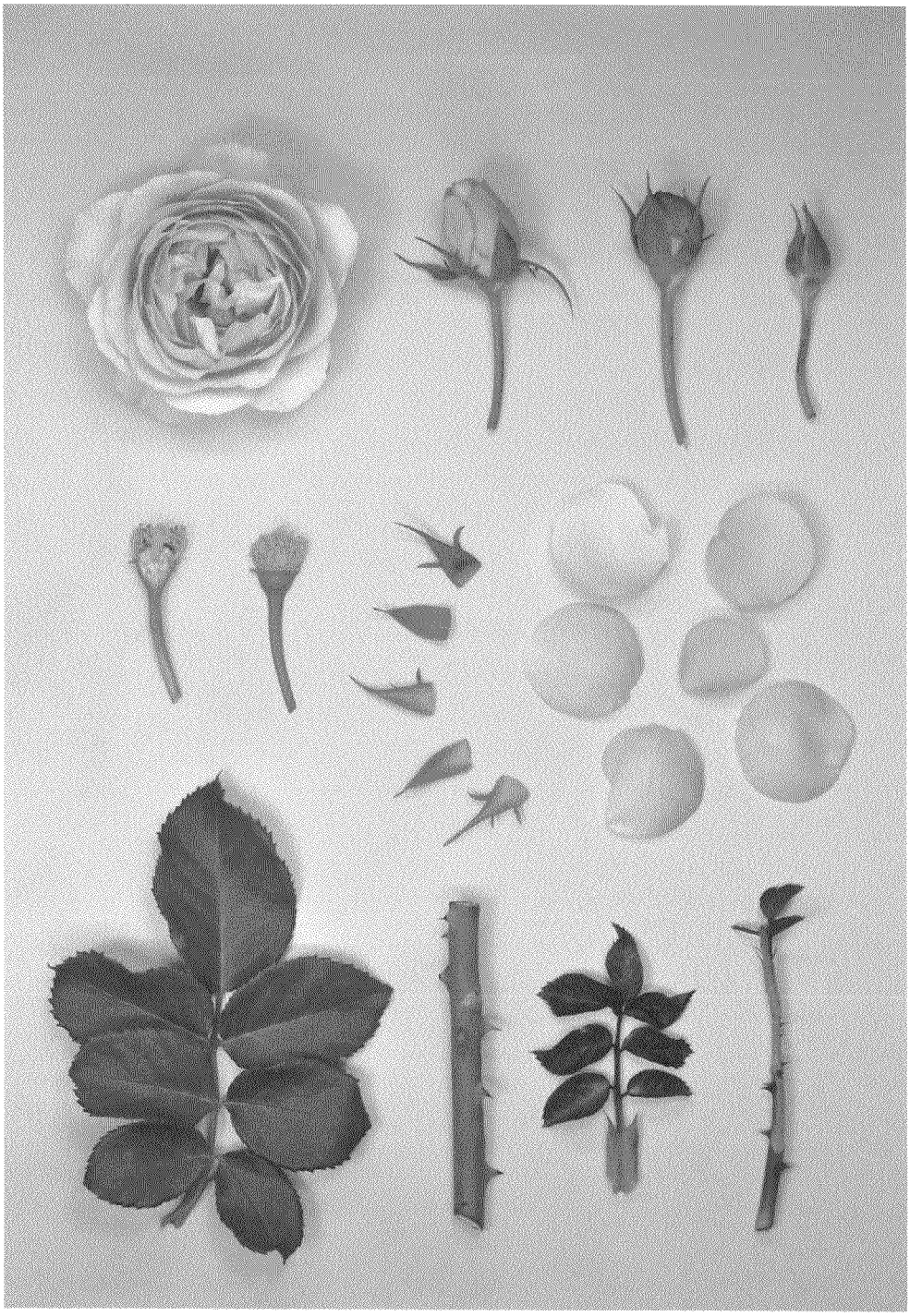

* * * * *